United States Patent [19]

Simonidesz et al.

[11] 4,330,553
[45] May 18, 1982

[54] 7-OXO-PGI$_2$-DERIVATIVES AND PROCESS FOR THE PREPARATION THEREOF AND PHARMACEUTICAL COMPOSITIONS CONTAINING SAME

[75] Inventors: Vilmos Simonidesz; Ágnes Papp née Béhr; Gábor Kovács; József Ivanics; Julia Dér née Földváry; Istvan Stadler; István Pallági, all of Budapest, Hungary

[73] Assignee: Chinoin Gyogyszer és Vegyészeti Termékek Gyára R.T., Budapest, Hungary

[21] Appl. No.: 205,292

[22] Filed: Nov. 10, 1980

[30] Foreign Application Priority Data

Nov. 12, 1979 [HU] Hungary .............................. CI-1978
Nov. 12, 1979 [HU] Hungary .............................. CI-1988

[51] Int. Cl.$^3$ .................. A61K 31/34; C07D 307/935; A61K 31/557
[52] U.S. Cl. .................................... 424/285; 542/420; 542/426; 542/429; 549/214; 549/414; 549/465
[58] Field of Search ...................... 260/346.22, 346.73; 542/420, 429, 426; 424/285

[56] References Cited

PUBLICATIONS

Simonidesz et al., J.A.C.S. 100, p. 6756, (1978).

Primary Examiner—Henry R. Jiles
Assistant Examiner—Bernard Dentz
Attorney, Agent, or Firm—Karl F. Ross

[57] ABSTRACT

New PGI$_2$ derivatives and a process for their preparation are disclosed of the formula (I)

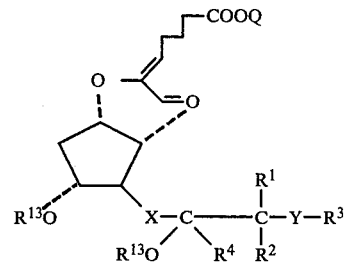

wherein

Q is hydrogen, a pharmacologically acceptable cation, or lower alkyl;

A is cis or trans —CH=CH—, —C≡C—, or —CH$_2$—CH$_2$—;

R$^{13}$ is hydrogen or a C$_1$ to C$_4$ alkanoyl or is a blockinggroup of the formula R$^7$R$^8$R$^9$Si or

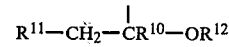

wherein R$^7$, R$^8$ and R$^9$ are the same or different and can be straight or branched chain alkyl groups having 1 to 4 carbon atoms and R$^{10}$ and R$^{11}$ are the same or different and can be hydrogen or methyl, and R$^{12}$ represents methyl or ethyl, or is tetrahydropyran-2-yl;

R$^4$ is hydrogen or lower alkyl inthe α or β steric position;

R$^1$ and R$^2$ are each hydrogen or lower alkyl;

Y is methylene, oxygen or an —NH— group; and

R$^3$ is lower alkyl or phenyl which can be monosubstituted phenyl. The compounds are useful as antiaggregation or thrombus-dissolving agents, stomach juice secretion inhibiting agents and antiasthmatic agents.

29 Claims, No Drawings

7-OXO-PGI₂-DERIVATIVES AND PROCESS FOR THE PREPARATION THEREOF AND PHARMACEUTICAL COMPOSITIONS CONTAINING SAME

The present invention relates to new optically active or racemic 7-oxo-PGI₂-derivatives of the formula I

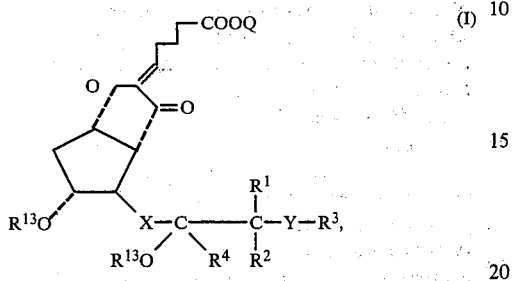

wherein

Q is hydrogen, a pharmacologically acceptable cation or lower alkyl,

X is cis or trans —CH=CH—, —C≡C— or —CH₂—CH₂—, $R^{13}$ is hydrogen or a $C_{1-4}$ alkanoyl or a blocking group of the formula $R^7R^8R^9Si$ or

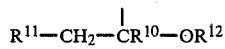

wherein $R^7$, $R^8$ and $R^9$ are the same or different and can be straight or branched chain alkyl groups having 1 to 4 carbon atoms and $R^{10}$ and $R^{11}$ are the same or different and can be hydrogen or methyl, and $R^{12}$ represents methyl or ethyl, or a tetrahydropyran-2-yl group, $R^4$ is hydrogen, or lower alkyl in α or β steric position, $R^1, R^2$ are hydrogen or lower alkyl, Y is methylene, oxygen or a —NH—group, $R^3$ is lower alkyl or phenyl or heteroaryl which can be mono-substituted, and to a process for the preparation thereof.

The new biologically active compounds of the formula I may be considered as stabilized analogs of the extremely potent PGI₂ of natural origin. PGI₂ (prostacycline) was first disclosed in Nature 263, 663 (1976). PGI₂ is one of the most valuable links of the arachidonic acid metabolism, being active in a very small amount. The most important pharmacological activity of the compound is its anti-aggregation and hypotensive activity. Even nanograms of PGI₂ inhibit the aggregation of the thrombocytes and dissolve already aggregated thrombi. Due to its unique pharmacological activity PGI₂ may be an outstanding pharmacological in treating the disease of our century, thrombosis and abnormal haemostasis. Numerous articles have been published about the clinical use of the substance.

The most important problem of the employment of PGI₂ as a pharmacological is the instability of the substance in an acidic or neutral medium in which it immediately decomposes to 6-keto-PGF₁α being in equilibrium with the hemiketal form thereof. PGI₂ contains a very reactive enol-ether structural unit, reacting immediately with an external or internal proton source. PGI₂ in the form of a free acid is thus unstable and therefore its salts and esters are employed in clinical and pharmacological tests.

The object of the invention is to provide new stable PGI₂ analog, which do not have the unstable character of natural PGI₂ preventing its pharmaceutical application, but preserve its therapeutical, mainly thrombocyte aggregation inhibiting and thrombolytic activity.

It has now been found that the new optically active or racemic 7-oxo-PGI₂ derivatives of the formula I are more stable than the known PGI₂ derivatives and possess valuable PGI₂ therapeutic activity.

In the definition of Q the pharmacologically acceptable cation may be an organic or inorganic cation which does not show any toxic effect in the employed amount. As inorganic cations, ions of alkali metals such as sodium, potassium or alkaline earth metals, such as calcium, magnesium can be used.

As suitable cations the unsubstituted ammonium ion or the ammonium ion substituted by organic groups preferably by alkyl groups may be mentioned as well. The substituents of the substituted ammonium ions can bear further substituents such as hydroxy groups or amino groups in order to affect a favorable influence upon the solubility and crystallization properties of the salts. For example tris-hydroxymethyl ammonium ion may be mentioned.

The straight and branched chain lower alkyl groups can contain 1 to 6 alkyl groups such as methyl, ethyl, n- and iso-propyl, n-, sec., tert. and iso-butyl and various pentyl and hexyl groups. The most preferred representatives contain 1 to 4 carbon atoms.

The $R^6$ hydroxy-blocking groups are well known in the prostaglandin chemistry. The blocking groups for the hydroxyl group may be introduced and cleaved by methods known per se. The hydroxy groups should be blocked in order to oxidize the hydroxy group selectively at the 7-position when oxidizing compounds of the formula VI

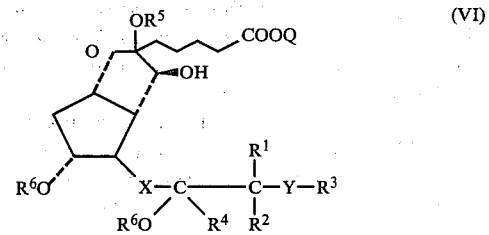

The blocking groups may be eliminated after the last elimination step or after oxidation.

Mono-substituted phenyl and substituted heteroaryl groups in the definition of $R^3$ may stand for groups bearing one or more same or different substituents selected from the group of lower alkyl optionally substituted by one or more halogen atoms and hydroxyl, sulfhydryl, lower alkanoyloxy, benzoyloxy, amino, mono- or di(lower alkyl) amino, halogen, lower alkoxy and lower alkylthio. Heteroaryl groups may contain one or more same or different heteroatoms such as nitrogen, oxygen and/or sulphur atom and consist of a 5 or 6 membered heteroaromatic ring optionally condensed with a benzene ring.

The compounds of the formula I can be prepared by using compounds of the formula III

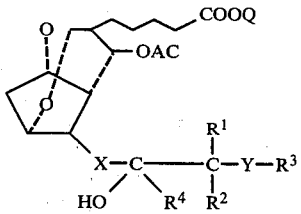

(III)

as starting materials—wherein $R^1$, $R^2$, $R^3$, $R^4$, X, Y and Q are defined above and Ac stands for acetyl. The compounds of the formula III are known (J. Am. Chem. Soc. 100, 6756, 1978) or can be prepared from corresponding starting materials by the method disclosed in the above cited reference.

According to the present invention compounds of the formula III are reacted with a lower aliphatic alcohol, preferably methanol, in the presence of an acid catalyst in traces at a temperature ranging from $-78°$ C. to $\pm 20°$ C. As acid catalyst mineral acids, sulfonic acids or Lewis acids are preferred. Particularly borontrifluoride etherate is preferred. Isomer ketals of the formula IV

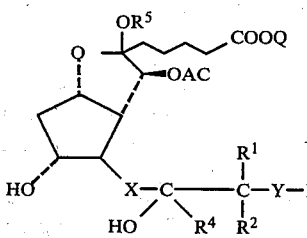

(IV)

wherein $R^5$ is lower alkyl—obtained in the above reaction may be further reacted in the form of their mixtures at an optional ratio or separated by chromatography.

In order to conduct a selective deacylation of the 7-acetoxy group and a selective oxidation of the obtained hydroxyl group, the free hydroxyl groups of the obtained compound of the formula IV are blocked provisionally in a basic and alkaline medium with stable blocking groups.

According to the invention compounds of the formula IV may be reacted with any reactant giving the above described blocking groups. Preferably (a) silylating agents of the formula VII

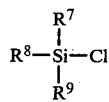

(VII)

wherein $R^7$, $R^8$ and $R^9$ are the same or different and may stand for straight or branched chain alkyl groups having 1 to 4 carbon atoms—or (b) enol ethers of the formula VIII

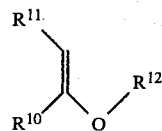

(VIII)

wherein $R^{10}$ and $R^{11}$ stand for the same or different substituents selected from hydrogen and methyl and $R^{12}$ represents methyl or ethyl—or (c) 3,4-dihydro-2H-pyran are employed.

As silylating agents of the formula VII trialkyl-chloro-silanes such as dimethyl-tert.butyl chloro-silane, trimethyl-chloro-silane can be employed. Dimethyl-tert.butylchlorosilane is preferably used in aprotic solvents, preferably in dimethylformamide in the presence of catalysts, preferably imidazole and trimethyl-chlorosilane may be used in pyridine or in aprotic solvents in the presence of tertiary amines. The reaction temperature can vary within a wide range, preferably between $-20°$ C. to $+60°$ C.

As enol ethers of the formula VIII preferably ethyl-vinyl-ether, isopropenyl methyl ether is employed in aprotic solvents, preferably in dichloromethane in the presence of a catalytic amount of acid. As suitable catalysts mineral acids, phosphoryl-chloride, sulfonic acids, preferably p-toluene sulfonic acid may be mentioned. The reaction temperature may vary within a wide range ranging from $-78°$ C. to $+50°$ C.

One may proceed similarly with 3,4-dihydro-2H-pyran as given for enol ethers of the formula VIII.

The compound of the formula V

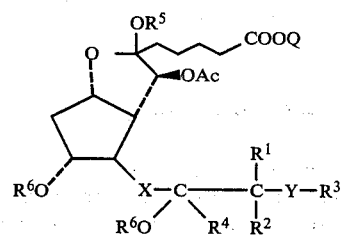

(V)

obtained in the above reactions and containing a blocked hydroxyl group—wherein $R^1$, $R^2$, $R^3$, $R^4$, $R^5$, X, Y, Ac and Q are as defined above and $R^6$ stands for a silyl group of the formula $R^7R^8R^9Si$ or α-alkoxyalkyl of the formula

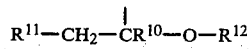

$$R^{11}-CH_2-CR^{10}-O-R^{12}$$

or a tetrahydropyran-2-yl group—wherein $R^7$, $R^8$, $R^9$, $R^{10}$, $R^{11}$, and $R^{12}$ are as defined above—may be hydrolyzed in a basic medium to provide compounds of the formula VI

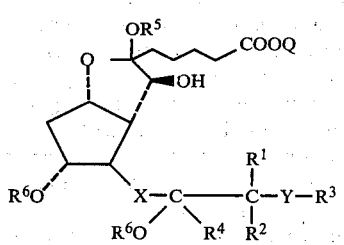

(VI)

The hydrolysis of the acetyl group may be conducted in lower alkanols, preferably in methanol, by using weak bases, preferably potassium carbonate or aqueous solutions of alkali or alkali earth metal hydroxides. In the latter case the carboxylic acids isolated from the reaction mixture are again converted to lower alkyl esters, preferably to the methyl ester by using preferably diazo-alkane. The reaction temperature is ranging from 0° C. to the boiling point of the employed solvents, one may perform the reaction preferably at room temperature. A longer reaction time and a stronger basic mixture may result that the alkyl in the position of $R^5$ will be so replaced by hydrogen.

The compounds of the formula VI wherein $R^5$ is hydrogen or lower alkyl may be oxidized with any oxidizing agent capable of oxidizing a secondary hydroxyl group to oxo group such as Jones reactant, Collins reactant, thioanizole chloro-complex, pyridinium chlorochromate etc. in aprotic solvents preferably in chlorinated hydrocarbons. The reaction temperature may vary in the range of $-40°$ C. to $+50°$ C.

The substituents of 7-oxo derivatives of the formula

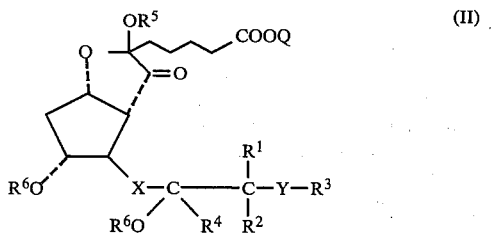

obtained in the above oxidation are as defined for the compounds of the formula VI.

The oxidation may also be conducted with compounds of the formula VI, wherein $R^5$ stands for hydrogen. In this case the secondary hydroxy group is selectively oxidized and thus hemiketal derivatives of the formula II are obtained which contain hydrogen in place of $R^5$. The obtained products may be further reacted or optionally converted again to derivatives of the formula II wherein $R^5$ is lower alkyl.

Blocking groups $R^6$ in the obtained compounds of the formula II can be cleaved and the free hydroxyl groups may be acylated with an alkanoyl group having 1 to 4 carbon atoms as well. In the last elimination reaction both compounds of the formula II containing free hydroxyl groups and $R^6$-blocked or acylated hydroxyl groups can be employed.

7-Oxo-PGI derivatives of the formula I are obtained from 7-oxo-derivatives of the formula II by eliminating a compound of the formula $R^5$—OH from these compounds.

Compounds of the formula I containing hydrogen as $R^{13}$ may be prepared from compounds of the general formula II wherein $R^5$ is lower alkyl and $R^6$ is hydrogen by eliminating the alcohol of the formula $R^5$—OH. The elimination of the alcohol may be performed by heating in various dipolar aprotic solvents such as dimethylformamide, dimethylsulfoxide, hexamethyl-phosphoric acid triamide.

The reaction temperature may be in the range from 70° C. to 180° C. The elimination may be accelerated by employing substances promoting elimination of alcohol, such as $C_{1-4}$ alkane anhydrides, benzene, toluene etc. When using acid anhydrides compounds of the formula I containing acyl as $R^{13}$ may also be formed the acyl groups of which may optionally be eliminated by base-catalyzed alcoholysis. Compounds of the formula I containing lower alkyl as Q can be isolated after purification for example by column chromatography.

Compounds of the formula I having a hydroxyl-blocking group $R^6$ as $R^{13}$ may be prepared from compounds of the formula II—wherein $R^5$ represents a lower alkyl group, $R^6$ stands for a hydroxy-blocking group by the elimination reaction described above. $R^6$ can be a hydroxyl blocking group, such as trialkyl-silyl or alkoxy-alkyl. Compounds of the formula I having a blocking group $R^6$ as $R^{13}$ may be isolated after purification by column chromatography and the blocking groups may optionally be cleaved, converting the products to compounds of the formula I having hydrogen as $R^{13}$. The trialkyl-silyl-blocking groups may be removed preferably with tetrabutyl ammonium fluoride in ether type solvents preferably in tetrahydrofuran at a temperature of $-20°$ C. to $+50°$ C., preferably at room temperature.

7-Oxo-PGI derivatives of the formula I may also be prepared from compounds of the formula II containing hydrogen as $R^5$ and the blocking group mentioned above as $R^6$ by eliminating the elements of water. The above compounds may be converted to compounds of the formula I having the above blocking groups as $R^{13}$ by boiling them in the presence of water binding agents in aromatic hydrocarbons. After removing the blocking groups compounds of the formula I containing lower alkyl as Q and hydrogen as $R^{13}$ may be purified, e.g. by chromatography.

Compounds of the formula I containing a pharmacologically acceptable cation as Q may be obtained from the corresponding esters of the formula I having a $C_{1-4}$ alkyl group as Q by aqueous alkaline hydrolyzing. As hydrolysing agent aqueous solutions of alkali and alkali earth metal hydroxides may be used at a temperature in the range of 0° C. to 100° C. and the salts are isolated for example after lyophilization. The carboxylic acids may be liberated from aqueous solutions of the salts by careful acidification and the acids can be converted to further salts by dissolving them in organic solvents and by reacting them with aliphatic and aromatic amines.

The new compounds of the formula I display, like the natural $PGI_2$, a thrombocyte-aggregation inhibiting and thrombolytic activity. The new compounds inhibit the synthesis of thromboxane $A_2$, inhibit the activity of thromboxane $A_2$ and the gastric juice secretion and act upon certain circulation processes. They may be used for the treatment of asthma, miocardial infarction, thrombosis, ulcer, vascular disorders in mammals, particularly in humans.

The pharmaceutical compositions containing as active ingredient 7-oxo-PGI derivatives of the formula I according to the invention can be employed to promote the thrombolysis of already established thrombosis and to prevent the formation of such thrombus. The prophylactic activity is of great significance in the preservation of blood, in perfusion of organs, tissues and in the elimination of the thrombus danger after operations.

$ID_{50}$ concentrations in case of aggregation generated with ADP and collagen resp. in plasma enriched with thrombocytes (PRB) isolated from human blood are as disclosed hereinbelow. As a comparison $ID_{50}$ concentration values obtained with $PGI_2$ sodium salt under the same test conditions are given.

Thrombocyte aggregation inhibiting activity:

| | $ID_{50}$(ng/ml) | |
|---|---|---|
| Substance inducing aggregation | ADP | collagen |
| Sodium salt of $PGI_2$ | 1–2 | 1–2 |
| Sodium salt of 7-oxo-$PGI_2$ | 15 | 80 |

| Substance inducing aggregation | ID$_{50}$(ng/ml) | |
|---|---|---|
| | ADP | collagen |
| 7-Oxo-PGI$_2$-methyl ester | 100–200 | 50 |

It is significant that the stomach fundus contracting activity is 0.1 times the activity of PGI$_2$.

The above data show that through the thrombocyte aggregation inhibiting activity of the compounds of the present invention is less effective than that of the natural PGI$_2$ but due to the stability of the compounds of the present invention in solution and due to the above documented high activity the compounds are particularly useful as active ingredients of pharmaceutical compositions. The dosage of 7-oxo-PG derivatives of the formula I will range from 100 ng to 100 mg per day depending on the effectivity to be achieved, on the route of administration, and on the sensitivity of the person, animal, organ or tissue to be treated.

In case of continuous infusion a daily dosage of 1–10 mg. is generally sufficient. The individual dosage may be determined by the physician without any difficulties on the basis of the intensity of the response of the patient.

Compounds of the formula I may be employed in conventional pharmaceutical formulations such as liquid, solid, semi-solid, paste or ointment forms. As liquid compositions, solutions, emulsions of injectable solutions, infusion solutions, drops and as solid compositions tablets, capsules, bolus, dragees, powders or powder vials may be mentioned. The preparations may contain the conventionally used fillers, diluents, additives influencing the osmotic pressure, pH, flavoring and aromatizing agents, lubricants, wetting agents, agents retarding dissolution, etc.

The present invention also provides pharmaceutical compositions and laboratory compositions containing as active ingredient 7-oxo-PGI derivatives as active ingredients as well as antiaggregation, anti-thrombosis, gastric acid secretion inhibition and antiasthmatic methods of treatment.

The further details of the invention may be found in the following Examples which serve merely for illustration and not limitation.

EXAMPLE 1

7β-Acetoxy-6-keto-PGF$_{1\alpha}$-methyl-ester-methyl-ketal (Formula IV wherein R$^5$ and Q stand for methyl, R$^1$, R$^2$ represent hydrogen, X stands for trans-vinyl, R$^4$ is hydrogen in β steric position, Y stands for methylene, R$_3$ is propyl.)

1 g. of a compound of the formula III—wherein the substituents are as given for the end product—is dissolved in 10 ml. of methanol and boron trifluoride etherate is added to the solution in catalytic amount. The reaction mixture is stirred for 20 minutes. After adding a small amount of solid sodium hydrogen carbonate methanol is distilled off in vacuo and the residue is dissolved in ethyl acetate. The ethyl acetate solution is washed subsequently with water and saturated aqueous sodium chloride solution, dried above anhydrous sodium sulphate, filtered and the solvent is distilled off. The residual oil is eluted on 120 g. of silica gel with ethyl acetate and thus 240 mg. (22%) exo-methyl-ketal and 680 mg. (63%) of endo-methyl-ketal are obtained in the form of a colorless oil.

exo-IV: R$_f$=0.31 developing agent: ethyl acetate $\delta^1$H NMR 3.64 (3H, COOCH$_3$), 3.24 (3H, OCH$_3$)

endo-IV: R$_f$=0.26 developing agent: ethyl acetate. $\delta^1$H NMR 3.57 (3H, COOCH$_3$), 3.14 (3H, OCH$_3$).

EXAMPLE 2

7β-Acetoxy-6-keto-PGF$_{1\alpha}$-methylester-methyl-ketal-11,15-bis(tert.butyl-dimethyl-silyl)-ether Formula V wherein R$^6$ stands for tert.butyl-dimethyl-silyl and the other substituents are as defined in Example 1.)

700 mg. (1.52 mmole) of a methyl-ketal of the formula IV obtained according to Example 1 are dissolved in 1.4 ml. of anhydrous dimethylformamide and 517 mg. (7.6 mmoles) of imidazole and 552 mg. (3.6 mmoles) of tert.butyl-dimethyl-chloro-silane are added to the solution. The reaction mixture is stirred for 4 hours at 35°–40° C., and poured on 30 ml. of water. The aqueous solution is extracted with 3×50 ml. dichloromethane and the combined dichloromethane extracts are washed with a saturated aqueous sodium chloride solution, dried with anhydrous sodium sulphate, filtered, and the solvent is distilled off. The residual oil is chromatographed on 120 g. of silicagel with a 8:1 mixture of hexane and ethyl acetate. Thus 788 mg. (75%) of title product are obtained in the form of colorless oil. R$_f$: 0.42 developed with a 7:1 mixture of hexane and ethyl acetate.

$^1$H NMR: 2.05 (3H, OAc), 0.88 (6H, tert.butyl).

EXAMPLE 3

7β-Hydroxy-6-keto-PGF$_{1\alpha}$-methylester-methyl-ketal-11,15-bis(tert.butyl-dimethyl-silyl)-ether (Formula VI wherein the substituents are as defined in Example 2.) formula V according to Example 2 are dissolved in 2 ml. of methanol and a catalytic amount of freshly calcinated potassium carbonate is added to the solution. The reaction mixture is stirred for 1 hour at room temperature. The solvent is distilled off in vacuo, the residue is dissolved in ethyl acetate, washed with saturated aqueous sodium chloride solution, dried above sodium sulphate, filtered and the solvent is stripped off. The residual oil is chromatographed on 20 g. of silicagel and eluted with a 4:1 mixture of hexane and ethyl acetate. Thus 150 mg. (80%) of the named compound are obtained in the form of colorless oil. R$_f$: 0.5 developing agent: 4:1 mixture of hexane and ethyl acetate.

IR (film) 3350 cm$^{-1}$ (OH).

EXAMPLE 4

7β-Hydroxy-6-keto-PGF$_{1\alpha}$-methylester-hemiketal-11,15-bis(tert.butyl-dimethyl-silyl)-ether (Formula VI wherein R$^5$=hydrogen, the other substituents are defined in Example 2.)

200 mg. (0.29 mmole) of silyl ether according to Example 2 of the formula V are dissolved in 2 ml. of methanol and 50 mg. of freshly calcinated potassium carbonate are added. The reaction mixture is stirred at room temperature for 48 hours. The reaction mixture is further processed according to Example 3. The crude product is chromatographed on 20 g. of silicagel with a 2:1 mixture of hexane and ethyl acetate. Thus 113 mg. (60%) of the named compound are obtained in the form of colorless oil. R$_f$: 0.1 developed with a 4:1 mixture of hexane and ethyl acetate.

$^1$H NMR: 3.67 (3H, COOCH$_3$).

EXAMPLE 5

7-Oxo-6-keto-PGF$_{1\alpha}$-methylester-methylketal-11,15-bis(tert.butyl-dimethyl-silyl)-ether (Formula II wherein R$^5$ stands for methyl and the other substituents are as defined in Example 2.)

75 mg. (0.11 mole) of a compound of the formula VI (product of Example 3), are dissolved in 0.7 ml. of dichloromethane and 63 mg. (0.29 mmole) of pyridinium chlorochromate are added to the solution.

The reaction mixture is treated with sodium acetate buffer, whereafter the mixture is stirred for 5 hours at room temperature. The reaction mixture is filtered, washed with dichloromethane and the combined filtrate is evaporated. The residue is chromatographed on 10 g. of silica gel by eluting with a 12:1 mixture of hexane and ethyl acetate.

Thus 56 mg. (75%) of the named compound are obtained in the form of colorless oil. R$_f$: 0.59 developed with a 7:1 mixture of hexane and ethyl acetate.

IR (film): 1735 cm$^{-1}$ (C=O), 1000–1250 cm$^{-1}$ (O—C—O).

EXAMPLE 6

7-Oxo-6-keto-PGF$_{1\alpha}$-methylester-hemiketal-11,15-bis-(tert.butyl-dimethyl-silyl)-ether (Formula II wherein R$^5$ stands for hydrogen and the other substituents are as defined in Example 2.)

50 mg. (0.08 moles) of silyl ether of the formula VI according to Example 4—wherein R$^5$ is hydrogen—are dissolved in 0.5 ml. of dichloromethane and 45 mg. (0.21 mmole) of pyridinium chlorochromate are added. The reaction mixture is stirred for six hours at room temperature. The reaction mixture is then processed according to Example 5, and the crude product is chromatographed on 10 g. of silicagel and eluted with an 1:1 mixture of ethylacetate and hexane. Thus 37 mg. (75%) of the named compound are obtained in the form of colorless oil. R$_f$: 0.55 developed by an 1:1 mixture of ethyl acetate and hexane.

IR (film): 3300 cm$^{-1}$ (OH), 1730 cm$^{-1}$ (C=O)

EXAMPLE 7

7$\beta$-Acetoxy-6-keto-PGF$_{1\alpha}$-methylester-methylketal-11,15-bis(tetrahydro-pyran-2-yl)-ether (Formula V wherein R$^6$ is tetrahydropyran-2-yl and the other substituents are as disclosed in Example 1.)

570 mg. (1.24 mmole) of a compound of the formula IV according to Example 1 are dissolved in 5 ml. of anhydrous dichloromethane and 1.13 ml. (12.4 mmoles) of anhydrous 3,4-dihydro-2H-pyran and catalytic amount of p-toluene-sulfonic acid is added. The reaction mixture is stirred for 10 minutes at room temperature, diluted with 50 ml. of ethyl acetate and the ethyl acetate solution is subsequently washed with saturated aqueous sodium hydrogen carbonate solution, with water and again with saturated sodium chloride solution. The mixture is dried above anhydrous sodium sulphate, filtered and the solvent is distilled off.

Thus 831 mg. (crude product) of named product are obtained in the form of a pale yellow oil.

R$_f$: 0.53 developed by an 1:1 mixture of benzene and ethyl acetate.

IR (film): 1740 cm$^{-1}$ (C=O), 1000–1200 cm$^{-1}$ (O—CH—O).

The named compound prepared as disclosed above may be reacted in the next reaction without purification.

EXAMPLE 8

7$\beta$-Hydroxy-6-keto-PGF$_{1\alpha}$-methylester-methylketal-11,15-bis(tetrahydropyran-2-yl)-ether (Formula VI wherein the substituents are as disclosed in Example 7.)

831 mg. (1.32 mmole) of a compound of the formula V obtained according to Example 7 are dissolved in 8 ml. of methanol and freshly calcined potassium carbonate in a catalytic amount is added to the solution. The reaction mixture is stirred for 1 hour at room temperature and processed according to Example 3. The residual oil is chromatographed with a 1:1 mixture of benzene and ethyl acetate on 40 g. of silicagel. Thus 471 mg. (65%) of named product are obtained in the form of colorless oil.

R$_f$: 0.35 developed with a 1:1 mixture of benzene and ethyl acetate

IR (film): 3350 cm$^{-1}$ (OH), 1735 cm$^{-1}$ (C=O). 1000–1200 cm$^{-1}$ (O—CH—O).

EXAMPLE 9

7-Oxo-6-keto-PGF$_{1\alpha}$-methylester-methylketal-11,15-bis(tetrahydropyran-2-yl)-ether (Formula II wherein the substituents are as disclosed in Example 7.)

344 mg. (0.59 mmole) of a compound of the formula VI obtained according to Example 8 are dissolved in 3.5 ml. of dichloromethane and 254 mg. (1.18 mmole) of pyridinium chlorochromate are added to the solution. The reaction mixture is treated with sodium acetate buffer whereafter the reaction mixture is stirred for 5 hours at room temperature. The reaction mixture is processed as described in Example 5. The crude product is chromatographed on 30 g. of silica gel with an 1:1 mixture of benzene and ethyl acetate.

275 mg. (80%) of the named compound are obtained in the form of a colorless oil.

R$_f$: 0.57 developed with a 1:1 mixture of benzene and ethyl acetate.

IR (film): 1730–1740 cm$^{-1}$ (C=O), 1000–1200 cm$^{-1}$ (O—CH—O)

EXAMPLE 10

7-Oxo-6-keto-PGF$_{1\alpha}$-methylester-methylketal (Formula II wherein R$^6$ stands for hydrogen and the other substituents are as described in Example 1.)

194 mg. (0.33 mole) of methyl ketal of the formula II according to Example 9—wherein R$^6$ is tetrahydropyranyl—and the other substituents are as defined for the title product, are dissolved in 10 ml. of methanol and catalytic amount of p-toluene-sulfonic acid is added to the reaction mixture. The solution is stirred for 1 hour at room temperature and the solvent is distilled off in vacuo. The residue is dissolved in ethyl acetate; the ethyl acetate solution is washed subsequently with saturated aqueous sodium hydrogen carbonate solution, with water and with saturated aqueous sodium chloride solution, dried above sodium sulphate, filtered and the solvent is distilled off.

The residual oil is chromatographed on 15 g. of silicagel with a 2:1 mixture of benzene and ethyl acetate.

Thus 117 mg. (85%) of the named compound is obtained in the form of colorless oil.

$R_f$: 0.34 developed with ethyl acetate.

$^1$H NMR (CDCl$_3$): 3.67 (COOCH$_3$), 3.17 (OCH$_3$)
IR(film): 3350 cm$^{-1}$ (OH), 1735 cm$^{-1}$ (C=O).

By using the corresponding substituted starting materials of the formula III the following intermediate products of the formula II may be prepared according to the processes described in Examples 1 to 10:

hemi ketal of 7-oxo-6-keto-16-methyl-PGF$_{1\alpha}$-methyl, ethyl-, propyl- and butyl esters and methyl ethyl-, propyl- and butyl ketals thereof;

hemi ketal of 7-oxo-6-keto-16,16-dimethyl-PGF$_{1\alpha}$-methyl-, ethyl-, propyl- and butyl ester and methyl-, ethyl-, propyl- and butylketal thereof;

hemi ketal of 7-oxo-6-keto-16-phenoxy-17,18,19,20-tetranor-PGF$_{1\alpha}$-methyl-, ethyl-, propyl- and butyl ester and methyl-, ethyl-, propyl and butylketal thereof;

hemi ketal of 7-oxo-6-keto-20-methyl-PGF$_{1\alpha}$-methyl-, ethyl-, propyl- and butyl ester and methyl-, ethyl-, propyl- and butylketal thereof;

hemi ketal of 7-oxo-keto-13,14-didehydro-PGF$_{1\alpha}$-methyl-, ethyl-, propyl- and butyl ester and methyl-, ethyl-, propyl- and butylketal thereof;

hemi ketal of 7-oxo-6-keto-15-methyl-PGF$_{1\alpha}$-methyl-, ethyl-, propyl and butyl ester and methyl-, ethyl-, propyl- and butylketal thereof;

hemi ketal of 7-oxo-6-keto-15-epi-PGF$_{1\alpha}$-methyl-, ethyl-, propyl- and butyl ester and methyl-, ethyl-, propyl- and butylketal thereof;

hemi ketal of 7-oxo-6-keto-15-epi-16,16-dimethyl-PGF$_{1\alpha}$-methyl-, ethyl-, propyl- and butyl ester and methyl-, ethyl-, propyl-, and butylketal thereof;

hemi ketal of 7-oxo-6-keto-15-epi-16-phenoxy-17,18,19,20-tetranor-PGF$_{1\alpha}$-methyl-, ethyl-, propyl- and butyl ester and methyl-, ethyl-, propyl- and butylketal thereof;

hemi ketal of 7-oxo-6-keto-15-epi-20-methyl-PGF$_{1\alpha}$-methyl-, ethyl-, propyl- and butyl ester and methyl-, ethyl-, propyl-, and butylketal thereof.

If in the course of the synthesis the blocking groups are not cleaved according to Example 10, then 11,15-bis-silyloxy-, 11,15-bis(tetrahydropyran-2-yl)- and 11,15-bis($\alpha$-alkoxyalkyl) derivatives of the above mentioned compounds are obtained (R$^6$ stands for silyl, tetrahydropyran-2-yl and $\alpha$-alkoxyalkyl).

The term "epi derivative" stands for a derivative in which at the position indicated by the number before "epi", the carbon atom has a substituent of opposite steric position than the corresponding carbon atom of the natural prostaglandine.

EXAMPLE 11

7-Oxo-PGI$_2$-methylester (Formula I wherein Q stands for methyl, R$^1$, R$^2$, R$^{13}$ stands for hydrogen, X stands for trans-vinyl, R$^4$ represents $\beta$ hydrogen, Y stands for methylene and R$^3$ represents propyl).

20 mg. (0.031 mmole) of a compound of the formula II according to Example 5 wherein R$^5$ stands for methyl, R$^6$ is dimethyl-tert.butyl-silyl and the other substituents stand for the same groups as defined for the title compound, are dissolved in 5 ml. of hexamethylphosphoric acid triamide. The reaction mixture is stirred for three hours at 150°–160° C. and poured on 18 ml. of water. The aqueous layer is extracted with 3×15 ml. of ethyl acetate and the combined ethyl acetate extract is washed with saturated sodium chloride solution, dried above anhydrous sodium sulphate, filtered and the solvent is distilled off. The residual 250 mg. of product are dissolved in 5 ml. of tetrahydrofuran and after adding 2 equivalents of tetrabutyl-ammonium-fluoride the mixture is stirred for 3 hours at room temperature. The solvent is distilled off in vacuo and the residue is dissolved in ethyl acetate. The ethyl acetate solution is washed with water, saturated aqueous sodium chloride solution dried above anhydrous sodium sulphate, filtered and the solvent is distilled off. The residual oil is chromatographed on 10 g. of silica gel with ethyl acetate. Thus 62 mg. (50%) of named compound are obtained in the form of colorless oil.

$R_f$: 0.44 developed by ethyl acetate.

$^1$H NMR: $\delta$5.37 (1H, t, O—C=CH—), 3.76 (3H, s, —COOCH$_3$).

EXAMPLE 12

7-Oxo-PGI$_2$-methyl ester 200 mg. (0.31 mmole) of a compound of the formula II according to Example 6—wherein R$^5$ stands for hydrogen, R$^6$ stands for dimethyl tert.butyl-silyl and the other substituents are as given in Example 11—are dissolved in 30 ml. of anhydrous benzene and the solution is heated for 2 hours in a Soxhlet extractor containing magnesium sulphate. The organic layer is washed with water and saturated aqueous sodium chloride solution, dried with anhydrous sodium sulphate, filtered and the solvent is distilled off. The crude product is treated with 2 equivalents of tetrabutyl ammonium fluoride in tetrahydrofuran and the reaction mixture is then processed as disclosed in Example 11. The product is chromatographed on 10 g. of silicagel and as eluting agent ethyl acetate was employed. Thus 52 mg. (45%) named product are obtained in the form of a colorless oil. The physical constants of the product are as given in Example 11.

EXAMPLE 13

7-Oxo-PGI$_2$-methyl ester 90 mg. (0.215 mmole) of 7-oxo-6-keto-PGF$_{1\alpha}$-methyl ester methyl ketal according to Example 10 (Formula II—wherein R$^5$ stands for methyl and R$^6$ is hydrogen) are dissolved in 0.8 ml. of hexamethyl-phosphoric acid-triamide and the reaction mixture is stirred for 2 hours at 140°–150° C. The reaction is processed according to Example 11. The residual oil is chromatographed on 10 g. of silica gel and eluted with ethyl acetate. Thus 40 mg. (47%) of the title compound are obtained in the form of a colorless oil. The physical constants of the product are as given in Example 11.

EXAMPLE 14

7-Oxo-PGI$_2$-methylester-11,15 diacetate (Formula I wherein R$^{13}$ stands for acetyl, Q stands for methyl, R$^1$, R$^2$ are hydrogen, R$^4$ stands for $\beta$ hydrogen, X represents trans-vinylene and Y stands for methylene.)

100 mg. of 7-oxo-6-keto-PGF$_{1\alpha}$-methylester-methylketal-11,15-diacetate are dissolved in 3 ml. of hexamethylphosphoric acid-triamide in the presence of 0.05 ml. of acetic acid anhydride and the solution is stirred for 2 hours at 80°–100° C. The reaction mixture is further processed according to Example 11. The crude product is chromatographed on 15 g. of silica gel and eluted with a 1:1 mixture of ethyl acetate and hexane.

Thus 70 mg. (70%) of the named compound is obtained in the form of a colorless oil. $R_f=0.65$ developed with a 1:1 mixture of ethyl acetate and hexane.

EXAMPLE 15

16,16-Dimethyl-7-oxo-PGI$_2$-methyl ester (Formula I where in $R^1$ and $R^2$ stand for methyl and the other substituents are as defined in Example 11.)

90 mg. (0.21 mmole) of 16,16-dimethyl-7-oxo-6-keto-PGF$_{1\alpha}$-methylester-methyl-ketal—wherein $R^1$ and $R^2$ stand for methyl- are dissolved in 1 ml. of hexamethylphosphoric acid-triamide and the reaction mixture is stirred for 2 hours at 140°–150° C.

The mixture is further processed according to Example 13.

Thus 50 mg. (56%) of the named compound are obtained in the form of a colorless oil.

$R_f$: 0.52 (in ethyl acetate).

EXAMPLE 16

Sodium salt of 7-oxo-PGI$_2$ (Formula I wherein Q stands for sodium and the other substituents are as defined in Example 11.)

50 mg. (0.13 mmole) of 7-oxo-PGI$_2$-methyl ester are dissolved in 0.1 ml. of methanol and 1.4 ml. of 0.1 N aqueous sodium hydroxide solution is added. When the addition is completed the reaction mixture is stirred for 24 hours at room temperature. The solution is lyophilized. Thus 55 mg. of the named compound are obtained in the form of a white mass.

Reactions according to Example 11 to 16 are repeated using as starting materials compounds of the formula II prepared according to Example 1 to 10; the following products are obtained:

7-Oxo-16-phenoxy-17,18,19-20-tetranor-PGI$_2$ and C$_{1-4}$ alkyl esters thereof ($R_f$ of methyl ester in ethyl acetate: 0.57);

7-Oxo-16-methyl-PGI$_2$ and C$_{1-4}$ alkyl esters thereof ($R_f$ of methyl ester in ethyl acetate: 0.49);

7-Oxo-2-methyl-PGI$_2$ and C$_{1-4}$ alkyl esters thereof ($R_f$ of methyl ester in methyl acetate: 0.51);

7-Oxo-13,14-didehydro-PGI$_2$ and C$_{1-4}$ alkyl esters thereof ($R_f$ of methyl ester: in ethyl acetate: 0.47);

7-Oxo-15-methyl-PGI$_2$ and C$_{1-4}$ alkyl esters thereof ($R_f$ of methyl ester in ethyl acetate: 0.53);

7-Oxo-15-epi-PGI$_2$ and C$_{1-4}$ alkyl esters thereof ($R_f$ of methyl ester in ethyl acetate: 0.50);

7-Oxo-15-epi-16,16-dimethyl-PGI$_2$ and C$_{1-4}$ alkyl esters thereof ($R_f$ of methyl ester in ethyl acetate: 0.58);

7-Oxo-15-epi-16-phenoxy-17,18,19,20-tetranor-PGI$_2$ and C$_{1-4}$ alkyl esters thereof ($R_f$ of methyl ester in ethyl acetate: 0.63);

7-Oxo-15-epi-20-methyl-PGI$_2$ and C$_{1-4}$ alkyl esters thereof ($R_f$ of methyl ester in ethyl acetate: 0.55).

Free acids may be prepared by saponification as disclosed in Example 16 from an alkali metal salt such as sodium salt by acidifying the aqueous solution thereof with a strong organic or inorganic acid. The free acid precipitates from the solution.

We claim:

1. An optically active or racemic 7-oxo-PGI$_2$ compound of the formula I

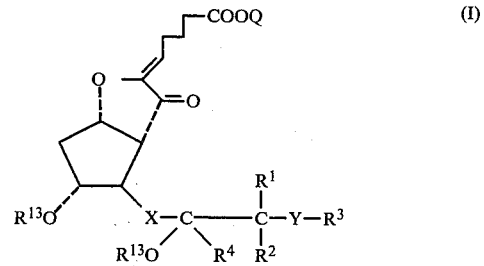

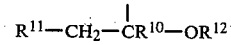

wherein

Q is hydrogen, a pharmacologically acceptable cation or lower alkyl

X is cis- or trans—CH=CH— or C≡C or —CH$_2$—CH$_2$—

$R^{13}$ is hydrogen or C$_{1-4}$ alkanoyl or a blocking group of the formula $R^7R^8R^9$Si or $$R^{11}-CH_2-\overset{|}{C}R^{10}-OR^{12}$$

wherein $R^7$, $R^8$, $R^9$ are the same or different and are straight or branched chain, C$_{1-4}$ alkyl groups, $R^{10}$ and $R^{11}$ represent the same or different groups selected from hydrogen and methyl and $R^{12}$ stands for methyl or ethyl, or is a tetrahydropyran-2-yl group, $R^4$ is hydrogen or lower alkyl in $\alpha$- or $\beta$-position, $R^1$ and $R^2$ stand for hydrogen or lower alkyl, Y is methylene, oxygen or —NH—, and $R^3$ is lower alkyl or phenyl which can be monosubstituted phenyl.

2. 7-Oxo-PGI$_2$-methylester as defined in claim 1.

3. 7-Oxo-PGI$_2$-methylester-11,15-diacetate as defined in claim 1.

4. 16,16-Dimethyl-7-oxo-PGI$_2$-methylester as defined in claim 1.

5. Sodium salt of 7-oxo-PGI$_2$ as defined in claim 1.

6. 7-Oxo-16-phenoxy-17,18,19,20-tetranor-PGI$_2$-methyl ester as defined in claim 1.

7. 7-Oxo-16-methyl-PGI$_2$-methylester as defined in claim 1.

8. 7-Oxo-20-methyl-PGI$_2$-methylester as defined in claim 1.

9. 7-Oxo-13,14-didehydro-PGI$_2$-methylester as defined in claim 1.

10. 7-Oxo-15-methyl-PGI$_2$-methylester as defined in claim 1.

11. 7-Oxo-15-epi-PGI$_2$-methylester as defined in claim 1.

12. 7-Oxo-15-epi-16,16-dimethyl-PGI$_2$-methylester as defined in claim 1.

13. 7-Oxo-15-epi-20-methyl-PGI$_2$-methylester as defined in claim 1.

14. 7-Oxo-15-epi-16-phenoxy-17,18,19,20-tetranor-PGI$_2$-methylester as defined in claim 1.

15. A process for the preparation of an optically active or racemic 7-oxo-PGI$_2$ compound of the formula I

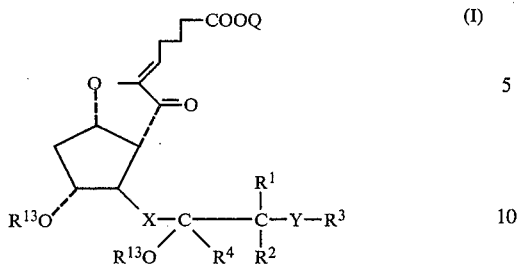  (I)

wherein
Q represents hydrogen, a pharmacologically acceptable cation or lower alkyl,
X stands for cis- or trans —CH=CH— or C≡C or —CH$_2$—CH$_2$—
$R^{13}$ represents hydrogen or $C_{1-4}$ alkanoyl or a blocking group of the formula $R^7R^8R^9Si$ or

wherein $R^7$, $R^8$ and $R^9$ are the same or different and stand for straight or branched chain, $C_{1-4}$ alkyl groups. $R^{10}$ and $R^{11}$ represent the same or different groups selected from hydrogen and methyl and $R^{12}$ stands for methyl or ethyl, or is a tetrahydropyran-2-yl group,
$R^4$ stands for hydrogen, or lower alkyl in α- or β-position,
$R^1$ and $R^2$ stand for hydrogen or lower alkyl,
Y represents methylene, oxygen or —NH—, and
$R^3$ stands for lower alkyl or optionally mono-substituted phenyl
which comprises
reacting a compound of the formula III

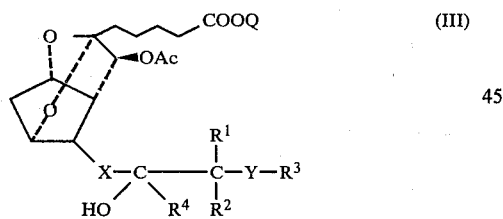  (III)

wherein Ac stands for acetyl—with a lower alkanol in the presence of a catalytic amount of an acid catalyst;
blocking the obtained ketal of the formula IV

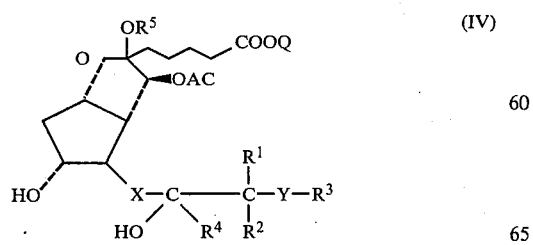  (IV)

wherein $R^5$ stands for lower alkyl—with a silylating agent of the formula VII

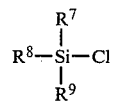  (VII)

or with an enol ether of the formula VIII

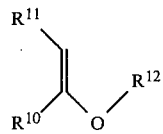  (VIII)

wherein $R^7$, $R^8$, $R^9$ are the same or different and stand for $C_{1-4}$ straight or branched chain alkyl, $R^{10}$ or $R^{11}$ are the same or different and stand for hydrogen or methyl and $R^{12}$ represents methyl or ethyl, or with 3,4-dihydro-2H-pyran;
deacetylating the obtained protected ketal of the formula V

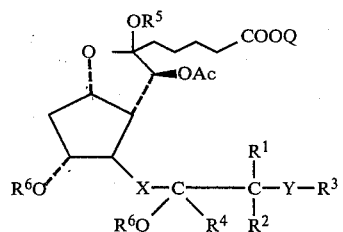  (V)

wherein $R^6$ represents a silyl group of the formula $R^7R^8R^9Si$ or a α-alkoxy-alkyl group of the formula

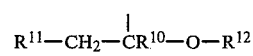

or a tetrahydropyran-2-yl group in a basic medium;
oxidizing the obtained blocked ketal containing a free hydroxy group of the formula VI

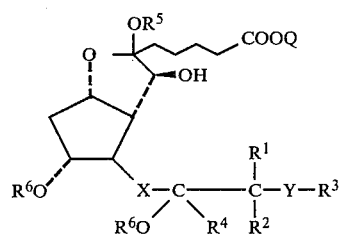  (VI)

in an aprotic solvent optionally after removing the $R^5$ lower alkyl substituent by hydrolysis to leave a free hydroxy group and
eliminating a compound of the formula $R^5$—OH— wherein $R^5$ stands for hydrogen or lower alkyl by heating the obtained 7-oxo-derivative of the formula II

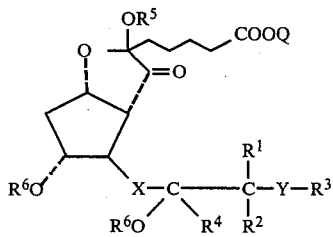

wherein $R^5$ stands for hydrogen or lower alkyl—optionally after removing blocking groups $R^6$ and optionally after the acylation of the free hydroxy groups with a lower alkanoyl group, and optionally eliminating blocking groups $R^{13}$ and/or saponifying the ester groups and forming salt from the free acid or forming ester.

16. A process as claimed in claim 15 which comprises using any of the starting materials selected from the compounds of the formulae III, IV, V, VI and II — and conducting the remaining synthesis steps.

17. A process as claimed in claim 15 which comprises performing the reaction of the compound of the formula III and a lower alkanol by using boron trifluoride etherate as an acid catalyst.

18. A process as claimed in claim 15 which comprises reacting a ketal of the formula IV—wherein $R^5$ stands for lower alkyl—with tert.butyl-dimethylchlorosilane.

19. A process as claimed in claim 15, which comprises reacting a ketal of the formula IV with 3,4-dihydro-2H-pyran.

20. A process as claimed in claim 15 which comprises performing the deacylation of the compound of the formula V with potassium carbonate.

21. A process as claimed in claim 15 which comprises oxidizing a blocked ketal containing a free hydroxy group of the formula VI with pyridinium-chlorochromate.

22. A process as claimed in claim 15 which comprises eliminating an alcohol of the formula $R^5$—OH— wherein $R^5$ stands for lower alkyl—from the 7-oxo-compound of the formula II by heating in hexamethylphosphoric acid triamide.

23. A process as claimed in claim 15 which comprises conducting the heating at 80°–160° C.

24. A process as claimed in claim 15 which comprises splitting off water from the 7-oxo-compound of the formula II—wherein $R^5$ stands for hydrogen by azeotropic distillation.

25. A process as disclosed in claim 24 which comprises conducting the azeotropic distillation in benzene, in the presence of anhydrous magnesium sulphate.

26. A pharmaceutical composition of anti-aggregation, thrombus dissolving, and stomach secretion inhibiting and anti asthmatic activity comprising an effective amount of at least one compound as defined in claim 1 and at least one formulation excipient.

27. An anti-aggregation- or thrombus-dissolving-method of treatment which comprises the step of administering to an animal subject in daily dosage per kg body weight 1 mg–10 mg of a compound as defined in claim 1.

28. A stomach juice secretion inhibiting-method of treatment which comprises the step of administering to an animal subject in daily dosage per kg body weight 1 mg–10 mg of a compound as defined in claim 1.

29. An anti-asthmatic method of treatment which comprises the step of administering to an animal subject in daily dosage per kg body weight 1 mg–10 mg of a compound as defined in claim 1.

* * * * *

UNITED STATES PATENT AND TRADEMARK OFFICE
CERTIFICATE OF CORRECTION

PATENT NO. : 4,330,553
DATED : 18 May 1982
INVENTOR(S) : Vilmos SIMONIDESZ et al It is certified that error appears in the above-identified patent and that said Letters Patent is hereby corrected as shown below:

In the abstract, item [57], right-hand column, please change formula (I) to read: --

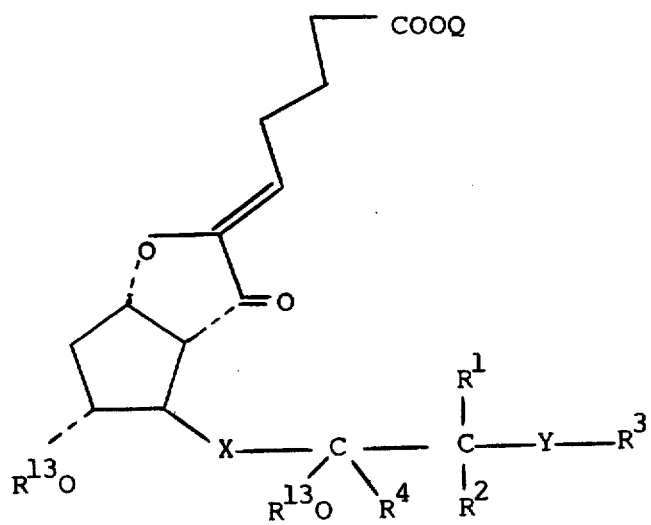

-- .

UNITED STATES PATENT AND TRADEMARK OFFICE
CERTIFICATE OF CORRECTION

PATENT NO. : 4,330,553
DATED : 18 May 1982
INVENTOR(S) : Vilmos SIMONIDESZ et al It is certified that error appears in the above-identified patent and that said Letters Patent is hereby corrected as shown below:

Column 1, change formula I to read: --

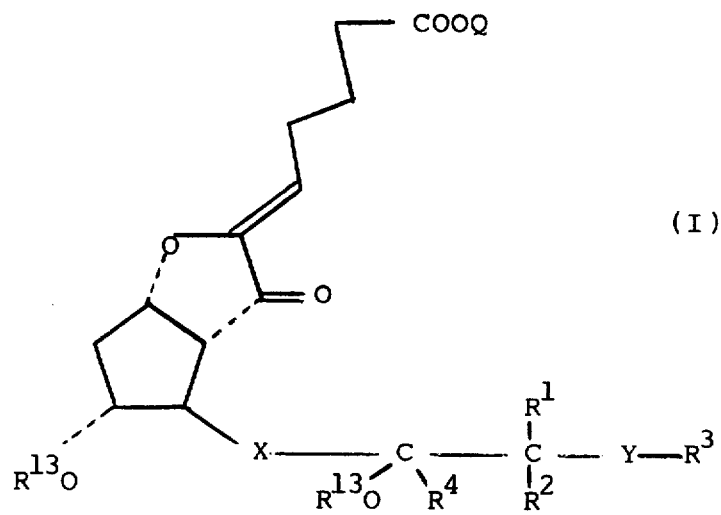

(I)

--.

UNITED STATES PATENT AND TRADEMARK OFFICE
CERTIFICATE OF CORRECTION

PATENT NO. : 4,330,553

DATED : 18 May 1982

INVENTOR(S) : Vilmos SIMONIDESZ et al

It is certified that error appears in the above-identified patent and that said Letters Patent is hereby corrected as shown below:

Column 2, change formula VI to read: --

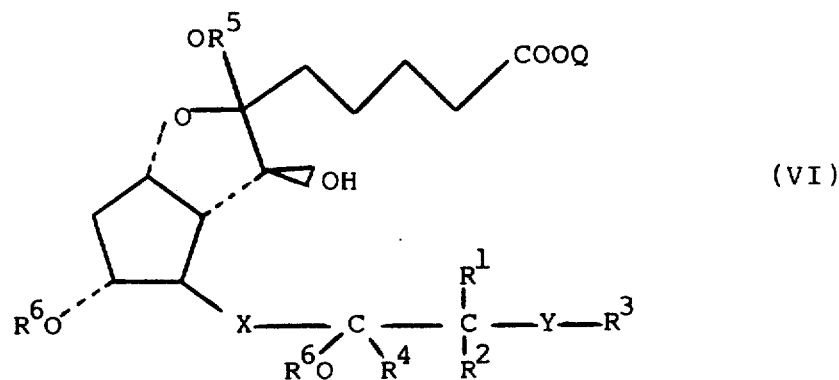

(VI)

--.

UNITED STATES PATENT AND TRADEMARK OFFICE
CERTIFICATE OF CORRECTION

PATENT NO. : 4,330,553

DATED : 18 May 1982

INVENTOR(S) : Vilmos SIMONIDESZ et al

It is certified that error appears in the above-identified patent and that said Letters Patent is hereby corrected as shown below:

Column 3, change formula III to read: --

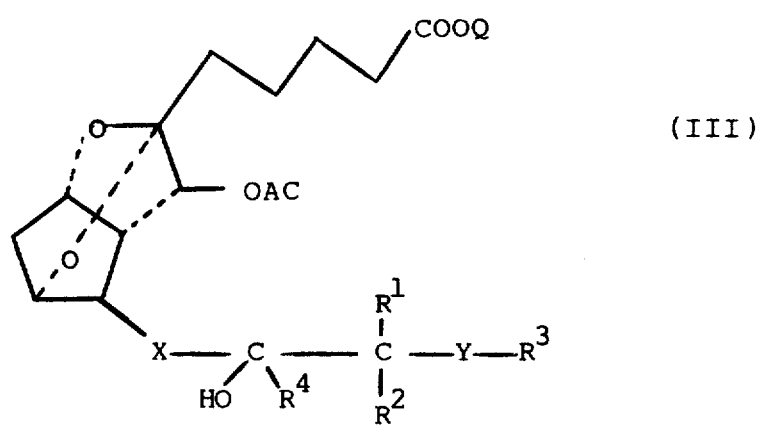

(III)

--.

UNITED STATES PATENT AND TRADEMARK OFFICE
CERTIFICATE OF CORRECTION

PATENT NO. : 4,330,553

DATED : 18 May 1982

INVENTOR(S) : Vilmos SIMONIDESZ et al

It is certified that error appears in the above-identified patent and that said Letters Patent is hereby corrected as shown below:

Column 15, change formula IV to read:

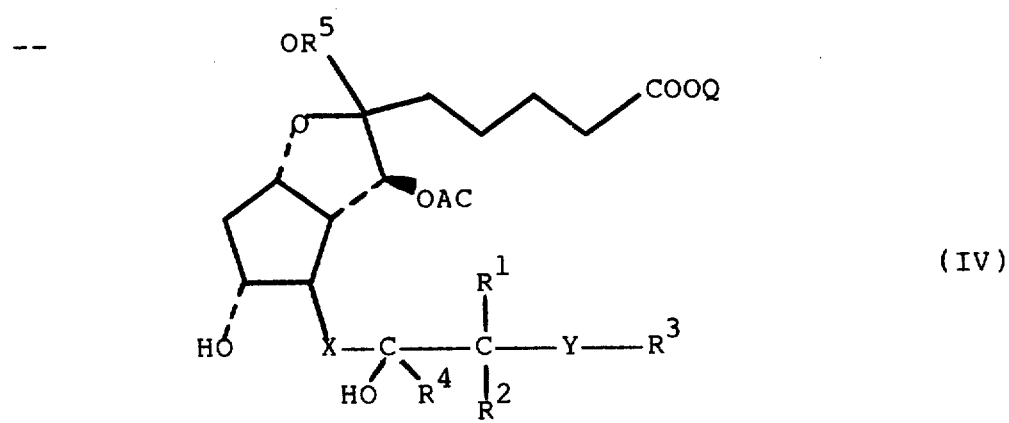

Signed and Sealed this

First Day of February 1983

[SEAL]

Attest:

GERALD J. MOSSINGHOFF

Attesting Officer   Commissioner of Patents and Trademarks